United States Patent [19]

Becher

[11] Patent Number: 6,153,222
[45] Date of Patent: *Nov. 28, 2000

[54] VOLUME-EXPANDABLE, SHEET-LIKE APPLICATION FORM SUITABLE AS AN ACTIVE SUBSTANCE CARRIER, IN PARTICULAR FOR ORAL APPLICATION

[75] Inventor: Frank Becher, Koblenz, Germany

[73] Assignee: LTS Lohmann Therapie - Systeme GmbH, Neuwied, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/765,117
[22] PCT Filed: Jun. 3, 1995
[86] PCT No.: PCT/EP95/02120
§ 371 Date: Dec. 6, 1996
§ 102(e) Date: Dec. 6, 1996
[87] PCT Pub. No.: WO95/33452
PCT Pub. Date: Dec. 14, 1995

[30] Foreign Application Priority Data

Jun. 7, 1994 [DE] Germany ............... 44 19 824

[51] Int. Cl.⁷ ................ A61K 7/00; A61K 7/16
[52] U.S. Cl. .............. 424/486; 424/401; 424/402; 424/405; 424/49
[58] Field of Search ................ 424/402, 486, 424/405, 49, 401

[56] References Cited

U.S. PATENT DOCUMENTS

| | | | |
|---|---|---|---|
| 4,699,146 | 10/1987 | Sieverding | 128/640 |
| 4,818,534 | 4/1989 | Levy | 424/404 |
| 5,344,641 | 9/1994 | Gaffer et al. | 424/49 |
| 5,368,844 | 11/1994 | Gaffar | 424/49 |

FOREIGN PATENT DOCUMENTS 4 018 247   5/1992   Germany .

*Primary Examiner*—Richard L. Raymond
*Attorney, Agent, or Firm*—Wenderoth, Lind & Ponack, L.L.P.

[57] ABSTRACT

A volume-expandable, sheet-like application form suitable as an active substance carrier, in particular for oral application, in the form of a film comprising a mixture of fillers, cleansers, cosmetics, or active substances, film formers, and softeners has portions of a highly absorbent hydrogel former which swells on contact with water and assumes several times its original volume.

12 Claims, No Drawings

VOLUME-EXPANDABLE, SHEET-LIKE APPLICATION FORM SUITABLE AS AN ACTIVE SUBSTANCE CARRIER, IN PARTICULAR FOR ORAL APPLICATION

The present invention relates to a volume-expandable, sheet-like application form suitable as an active substance carrier, in particular for oral application, in the form of a film comprising a mixture of fillers, cleansers, cosmetics, or active substances, film formers, and softeners.

Sheet-like substrates, in particular for oral administration, have been known for some time. A variety of advantages are achieved with such substrates, in particular light weight and low volume, which offer a number of advantages with respect to an ecological overall balance; they require less package and storage space, for example.

DE 40 18 247 describes a film-shaped, individually dosed administration form which rapidly disintegrates in water. It is used for drugs, sweets, other foodstuffs, cosmetics for oral application or intake, and comprises a base mass on a carrier, or consists of the base mass without carrier. It can be produced according to a method comprising the following steps:

a) film former, gel former, active substance, and filler are intimately premixed in dry condition;
b) the premix is stirred into a spreadable consistency under addition of up to 30% -wt. of a polar solvent; and
c) the mass so obtained is applied on a release film at a layer thickness ranging from 0.003 to 4 mm, preferably 20 to 400 $\mu$m, and most preferably 70 to 1 50 $\mu$m;
d) the polar solvent is removed, i.e., up to an amount required to fluidize the mass.

The disadvantage of such film-like administration forms is that the small size and lightness complicate ease of handling. If these drawbacks prior to removal from a suitable dispenser package may be overcome, there is still the problem that the taken product is not easy to handle. Providing the product with a tacky surface to overcome this deficiency, results in the disadvantage that handling prior to or during removal from a package or dispenser is rendered more difficult. Using suitable cover films as a remedial measure, results in the further drawback that advantages with respect to light weight, unproblematic disposal and production costs are compensated by additional process steps.

It is the object of the present invention to improve these difficult-to-handle, sheet-like and small substrates or application forms to obtain better handling with avoidance of the above-mentioned difficulties and technical limitations.

In a volume-expandable, sheet-like application form of the above-mentioned kind designated for the use as an active substance carrier, in particular for oral application, this object is achieved according to the present invention by the fact that it has portions of a highly absorbent hydrogel former swelling on contact with water and assuming several times its original volume.

This measure advantageously achieves that the substrate or application form increases its volume very quickly to a considerable extent on contact with a liquid medium, and thereby also obtains a certain tackiness. In this connection, the fact is used that contact with moisture during use is desired and necessary in a wide field of application for these substrates. According to the present invention the volume increase is achieved by using suitable swelling agents, for example, those known as so-called absorbent polymers in sanitary products, such as diapers, panty liners, in feminine hygiene, and the like. These are swellable substances which absorb aqueous liquids and spontaneously combine with them to form a relatively stable gel. They are capable of absorbing and permanently retaining many times their weight of aqueous liquids. The resultant gel has chain-like molecules linked into a three-dimensional network and embedded in a liquid medium.

According to one embodiment the film is coated with a highly absorbent hydrogel former.

The highly absorbent hydrogel former may also be incorporated into the film as a suspension component.

The highly absorbent hydrogel former is a polymer and preferably comprises cross-linked carboxyvinyl copolymers and/or cross-linked polyvinyl pyrrolidones.

Moreover, an additional effect may be achieved by the fact that the polymer comprises substance which are effervescent on contact with water. Such substances may be sodium bicarbonate, and citric or ascorbic acid, or other physiologically acceptable acids. If these foams are used, rapid disintegration of the sheet-like system, which is desirable in some cases, may selectively be further accelerated by the developing increase in volume.

In particular, this effect may favorably be used in a preparation for tooth brushing, namely a sheet-like dentifrice dosage form or "dentifrice wafer". In this case, volume increase and tackiness after removal are particularly desirable. By this, the preparation may be applied on the tooth brush like a tooth paste.

The risk of sliding down is considerably reduced. Moreover, the skilled artisan may designate a variant thereof for administration forms that are to be swallowed. In this case, the outer layer of a hydrogel may be formed such that it easily passes the gullet owing to the use of water-absorbing swelling agents and rapidly disintegrates in a later phase.

Example of a sheet-like system according to the present invention 24 g of a 17% (w/w) solution of polyvinyl pyrrolidone (e.g. Kollidon® 90) in ethanol is stirred with 5 g of a cross-linked carboxy-vinyl copolymer (Aquakeep® 10 SH) into a viscous suspension which is free from air bubbles. This mass is spread on siliconized paper at a gap width of 500 $\mu$m using a film-drawing frame. Drying for 5 minutes at 70° C. follows. The resultant film is removed from the release paper; compared to the comparative example it has a larger volume and an improved dimensional stability with a negligibly longer disintegration time.

Comparative Example 30 g of a 17% (w/w) solution of polyvinyl pyrrolidone (e.g. Kollidon® 90) in ethanol is spread on siliconized paper at a gap width of 500 $\mu$m using a film-drawing frame. Drying for 5 minutes at 70° C. follows. The resultant film is removed from the release paper.

Further Substances

Fillers: e.g., calcium sulfate, calcium carbonate, calcium phosphate, silica gel
Active substances: sodium fluoride, sodium monofluoro-phosphate
Foamers: sodium dodecylsulfonate, neutral surfactants
Film formers: polyvinyl alcohol, polyvinyl pyrrolidone
Flavoring agents
Softeners: polyethylene glycols, glycerol
Sweeteners: saccharose, cyclamates, saccharin.

What is claimed is:
1. In a volume-expandable application form for animal or human oral hygiene or oral treatment in the form of a film comprising a film former, a softener and at least one member selected from the group consisting of a filler, a cleanser, a cosmetic and an active ingredient, the improvement wherein the film contains portions of a highly absorbent cross-linked polymer hydrogel former which swells on contact with water to assume several times its original volume.

2. The application form according to claim 1, wherein the film is coated with the hydrogel former.

3. The application form according to claim 1, wherein the hydrogel former is incorporated into the film as a suspension component.

4. The application form according to claim 1, wherein the hydrogel former comprises a cross-linked carboxyvinyl copolymer and/or a cross-linked polyvinyl pyrrolidone.

5. The application form according to claim 1, wherein the hydrogel former also contains a substance which is effervescent upon contact with water.

6. The application form according to claim 5, wherein the effervescent substance is sodium bicarbonate with a physiologically acceptable acid.

7. The application form according to claim 6, wherein the physiologically acceptable acid is citric acid or ascorbic acid.

8. The application form according to claim 1, wherein the hydrogel former also contains an adhesive suitable for oral use.

9. The application form according to claim 8, wherein the adhesive is a starch adhesive.

10. The application form according to claim 1, wherein the filler is selected from the group consisting of calcium sulfate, calcium carbonate, calcium phosphate and silica gel; the active substance is selected from the group consisting of sodium fluoride, sodium monofluorophosphate; and the softener is selected from the group consisting of polyethylene glycol and glycerol.

11. The application form according to claim 1, further comprising a foamer, a flavoring agent or a sweetener.

12. The application form according to claim 11, wherein the foamer is selected from the group consisting of sodium dodecylsulfonate, and a natural surfactant; and the sweetener is selected from the group consisting of saccharose, cyclamates and saccharin.

* * * * *